(12) United States Patent
Ramkumar

(10) Patent No.: US 6,397,672 B1
(45) Date of Patent: Jun. 4, 2002

(54) METHOD FOR DETERMINING THE FRICTIONAL PROPERTIES OF MATERIALS

(75) Inventor: Seshardi S. Ramkumar, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 09/672,837

(22) Filed: Sep. 29, 2000

(51) Int. Cl.⁷ ................................................. G01L 5/04
(52) U.S. Cl. ..................... 73/159; 73/7; 73/9
(58) Field of Search ................... 73/7, 9, 159

(56) References Cited

U.S. PATENT DOCUMENTS

| | | |
|---|---|---|
| 3,503,257 A | 3/1970 | McElhaney et al. |
| 3,688,558 A | 9/1972 | Tixier |
| 3,763,483 A | 10/1973 | Urmenyi |
| 3,977,231 A * | 8/1976 | Haehner et al. .......... 73/9 |
| 4,414,984 A | 11/1983 | Zarudiansky |
| 4,521,685 A | 6/1985 | Rebman |
| 4,555,953 A | 12/1985 | Dario et al. |
| 4,601,664 A | 7/1986 | Bertino, III et al. |
| 4,640,137 A | 2/1987 | Trull et al. |
| 4,748,672 A | 5/1988 | Nevill, Jr. et al. |
| 4,942,620 A | 7/1990 | Nevill, Jr. |
| 5,245,856 A * | 9/1993 | Pazzaglia et al. .......... 73/9 |
| 5,261,266 A | 11/1993 | Lorenz et al. |
| 5,373,747 A | 12/1994 | Ogawa et al. |
| 5,427,156 A | 6/1995 | Saito |
| 5,744,732 A | 4/1998 | Kubby et al. |
| 6,122,978 A * | 9/2000 | Callendrier ............ 73/862.474 |
| 6,145,382 A * | 11/2000 | Nagasawa et al. ............ 73/664 |

OTHER PUBLICATIONS

F.T. Peirce, "The 'Handle' of Cloth as a Measurable Quantitiy," The Journal of the Textile Institute Transactions, T377–T416, British Cotton Industry Research Association.
John Albert Morrow, "The Frictional Properties of Cotton Materials," The Journal of the Textiel Institute Transactions, T425–T440, British Cotton Industry Research Association.
Edwin C. Derby, "A Friction Meter for Determining the Coefficient of Kinetic Frication of Fabrics," Part of Journal of Reasearch of the National Bureau of Standards, vol. 31, Oct. 1943, 237–246, Department of Commerce.
H.G. Howell, "Inter Fiber Friction," Journal of the Textile Institute, vol. 42, 1951, T521–T535, Textile Institute.

(List continued on next page.)

Primary Examiner—Hezron Williams
Assistant Examiner—C D Garber
(74) Attorney, Agent, or Firm—Jones, Tullar & Cooper, PC

(57) ABSTRACT

The invention sets forth a method for determining the hand quality of a fabric or other material. The invention establishes a new constant value to be applied to this determination. The constant value is referred to as the Quality Energy Value (hereinafter the "QE value") of a material. The QE value takes into account the reciprocatory motion actually used when rubbing a piece of cloth with a finger to subjectively determine the hand quality of a fabric. The invention utilizes a testing apparatus which simulates this sliding motion of finger on fabric. The QE value also advantageously takes into account the velocity at which the frictional properties of the fabric are measured. It has been found that the lower the QE value, the better the quality of the fabrics. Accordingly, using the method of the invention, a range of QE values may be established for a variety of fabrics, and, thereby, the relative hand qualities of the fabrics may be compared.

5 Claims, 1 Drawing Sheet

OTHER PUBLICATIONS

H.G. Howell and J. Mazur, "Amontons' Law and Fibre Friction," Journal of the Textile Institute, vol. 44, 1953, T59–T69, Textile Institute.

D. Wilson, "A Study of Fabric–On–Fabric Dynamic Friction," Journal of the Textile Institute Transactions, vol. 54 No. 4, Apr. 1963, T143–T155, The Textile Institute and Contributers.

W.W. Carr Et Al., "Frictional Characteristics of Apparel Fabrics," Mar. 1988, 129–136, School of Textile Engineering, Georgia Institiute of Technology.

Joseph O. Ajayi, "Fabric Smoothness, Friction, and Handle," Textile Research Journal, 52–59, Department of Pure and Applied Chemistry, University of Strathclyde, Scotland Masayasu Ohsawa and Satoru Namiki, "Anisotropy of the Static Friction of Plain–woven Filament Fabrics," Jornal of Textile Machinery Society of Japan, vol. 19 No. 1, 1966, 197–203, Faculty of Technology, Tokyo University of Agriculture and Technology.

R. Chattopadhyay and S. Banerjee, "The Frictional Behavior of Ring–, Rotor–, and Friction–spun Yarn," 59–67, Department of Textile Technology, Indian Institute of Technology, New Delhi, India.

Dominique Dupuis Et Al., "Compression of Greystate Fabrics as a Function of Yarn Structure," 309–316.

S.C. Harlock and S.S. Ramkumar, "A Study of the Handle Characteristics of Cotton Rib Knitted Fabrics," Textiles and the Information Society, vol. 3, 149–161, Department of Textile Industries, University fo Leeds.

Witold Zurek Et A., "Surface Frictional Resistance of Fabrics Woven from Filament Yarns," 113–121, Textile Research Institute, Lodz, Poland.

Luis Virto and Arun Naik, Frictional Behavior of Textile Fabrics, Part 1: Sliding Phenomena of Fabrics on Metalic and Polymeric Solid Surfaces, 793–802, Terassa, Spain.

"Knitting and Apparel News," America's Textile International, Jun. 12, 1999.

Anndrea Vorobej, New and Analysis @ Textile Web (Mar. 2, 2000) <Http://.../article.asp?DocID={F3A56F8F–F053–11D3–8C24–009027DE0829}&Bucket=Feature>, Mar. 31, 2000, 1–2.

Textile Horizons, Sep. 14, 1999.

S.S. Ramkurmar and H. Ishikura, "Measuring theQuality of Textiles in the New Millennium," The 5th Asian Textile Conference, Sep. 30–Oct. 2, 1999, 530–533, TX, USA.

S.S. Ramkumar and H. Ishikura, "Measuring the Immeasurable: Is there a Pancea?," The 5th Asian Textile Conference, Sep. 30–Oct. 2, 1999, 562–565, TX, USA.

S.S. Ramkumar and H. Ishikura, "An Outline of the Research Activity on the Frictional Interaction Studies of Textile Fabrics of Human Skin and its Subsitutes," The 5th Asian Textiel Conference, Sep. 30–Oct. 2, 1999, TX, USA.

S.S. Ramkumar and H. Ishikura, "A Study of the Handle Characteristics of 1×1 Rib Cotton Weft Knitted Fabric," the 5th Asian Textile Conference, Sep. 30–Oct. 2, 1999, i–iii and 263–305, TX, USA.

Kara Altenbaumer, "Mechanical digit created with 'feeling'," Lubbock–Avalanche Journal, Mar. 16, 2000.

S.S. Ramkumar Et Al., "A Study of the Frictional Properties of 1×1 Rib Knitted Cotton Fabrics," Journal of Textiel Institute, Dec. 13, 1999, 1–15, Leeds, England.

S.S. Ramkumar, "The Wunderful World of Textiles," Lubbock Magazine, Apr. 2000, 58–61.

S.S. Ramkumar, "Artificial Human Finger for Friction Studies of Textiles," Daily News Record, Leeds, England.

Kevin McEwen, "Research develops finger to test fabrics," The University Daily, Apr. 4, 2000.

* cited by examiner

METHOD FOR DETERMINING THE FRICTIONAL PROPERTIES OF MATERIALS

BACKGROUND OF THE INVENTION

1. Field of the Invention

The present invention generally relates to a method for determining the frictional properties of materials, such as textiles, to better quantify values such as skin-feel, hand, and texture of the materials. While the invention is presented as being applied to textiles, the invention is also applicable to polymer films, paper sheets, and other surfaces.

2. Description of the Prior Art

Of the major aesthetical attributes of fabrics, the handle attribute is probably the most difficult to quantify. The handle or "hand" of a fabric refers to the suppleness, softness, smoothness, flexibility, and thickness of a fabric, and relates to a complex mechanism involving physical, psychological, and neurological concepts, which combine to produce a perceived quality of the fabric. The most common method for evaluating the hand of a fabric is a subjective analysis accomplished by a person rubbing the fabric between a thumb and forefinger. However, this method is far from ideal, and the subjective nature of the test makes it difficult to establish common industry-wide parameters regarding the hand of fabrics.

F. T. Peirce ("The Handle of Cloth as a Measurable Quantity", *J. Textile Inst*, 21, T377-T416 (1930)) pioneered attempts to explain the hand of fabrics in terms of their physical properties, and stressed the importance of the surface properties of the fabric. Pierce did not attempt to study and measure the surface properties, but the characterization of the frictional properties of textile materials has occupied other textile researchers for many years. For example, J. A. Morrow ("The Frictional Properties of Cotton Materials", *J. Textile Inst.*, 22, T425-T440 (1931)) measured the frictional properties of fabrics at different normal loads, areas of contact and speeds of testing, and proposed an empirical relationship of the form:

$$F=mP+kA \quad (1)$$

where F is the frictional force, P is the pressure, and A is the area of contact. It is immediately apparent from this equation that the commonly accepted Amontons Law for the coefficient of friction ($\mu=F/N$), first set forth by Guillaume Amontons, would not fit Morrows data. E. C. Dreby ("A Friction Meter for Determining the Coefficient of Kinetic Friction of Fabrics", *J. Research Nat. Bur. Standard*, 31, 237-246 (1943)) confirmed this conclusion, and a later investigation by H. G. Howell ("Inter-Fiber Friction", *J. Text Inst.*, 42, T521-T535 (1951)) provided further evidence that Amontons laws are not valid with respect to the frictional properties of fabrics.

Fundamental work by Howell and Mazur ("Amontbns Law and Fibre Friction", *J. Text Inst.*, 44, T59-T69 (1953)) suggested that a more suitable relationship for the frictional properties of fabric was of the form:

$$F=CP^n \quad (2)$$

where n is a frictional index $0<n<1$, F is the frictional force per unit area of contact, P is the normal force per unit area of contact, and C is a frictional constant. A thorough experimental investigation of this relationship was carried out by D. Wilson ("A Study of the Fabric-on-Fabric Dynamic Friction", *J. Textile Inst.*, 54,143-155 (1963)) that confirmed its suitability. More recently Carr et al. ("Frictional Characteristics of Apparel Fabrics", *Textile Res. J.*, 58,129-136 (1988)) and J. O. Ajayi ("Fabric Smoothness, Friction and Handle", *Textile Res. J.*, 62, 52-59 (1992)) have studied the effects of weave, fabric weight, direction of rubbing, etc. on the frictional properties of woven fabrics.

All of the foregoing authors attempted to define the hand quality or other properties of fabrics based upon friction constants, and with reference to Equation (2), the C value has become a well-known friction constant for quantifying the properties of fabrics. However, referring to earlier papers (Carr et al., 1988; Ajayi, 1992), where F and N are measured in physical pressure units (i.e., Pascals, which are Newtons/$m^2$, hereinafter "Pa"), and when solving Equation (2) for physical units, it is evident that n has no unit. However, the friction constant C has a unit $Pa^{(1-n)}$. Thus, it is evident from the foregoing discussion that the friction constant C is dependent on n. This dependency causes difficulty in comparing the C values of different fabrics. Furthermore, because n is a measure of the physical characteristics of the material, n values tend to vary from material to material. Thus, it is not logical to compare and characterize the frictional properties of two different textile materials using the C values. Accordingly, it is desirable to establish a new method and apparatus for quantifying the quality of a fabric or other material.

SUMMARY OF THE INVENTION

In the preferred form, the invention sets forth a method for determining the quality of a fabric or other material. The invention establishes a new constant value to be applied to this determination. The constant value is referred to as the Quality Energy Value (hereinafter the "QE value") of a material. The QE value takes into account the reciprocatory motion actually used when rubbing a piece of cloth with a finger, and utilizes a testing apparatus which somewhat simulates this to and fro motion. The QE value also advantageously takes into account the velocity at which the frictional properties of the fabric are measured. As will be demonstrated in more detail below, it has been found that the lower the QE value, the better the quality of the fabrics. Accordingly, using the method of the invention, a range of QE values may be established for a plurality of fabrics, and, thereby, the relative qualities of the fabrics may be compared.

BRIEF DESCRIPTION OF THE DRAWINGS

The foregoing and additional objects, features, and advantages of the present invention will become apparent to those of skill in the art from a consideration of the following detailed description of preferred embodiments of the invention, taken in conjunction with the accompanying drawings.

DETAILED DESCRIPTION

Figure 1:
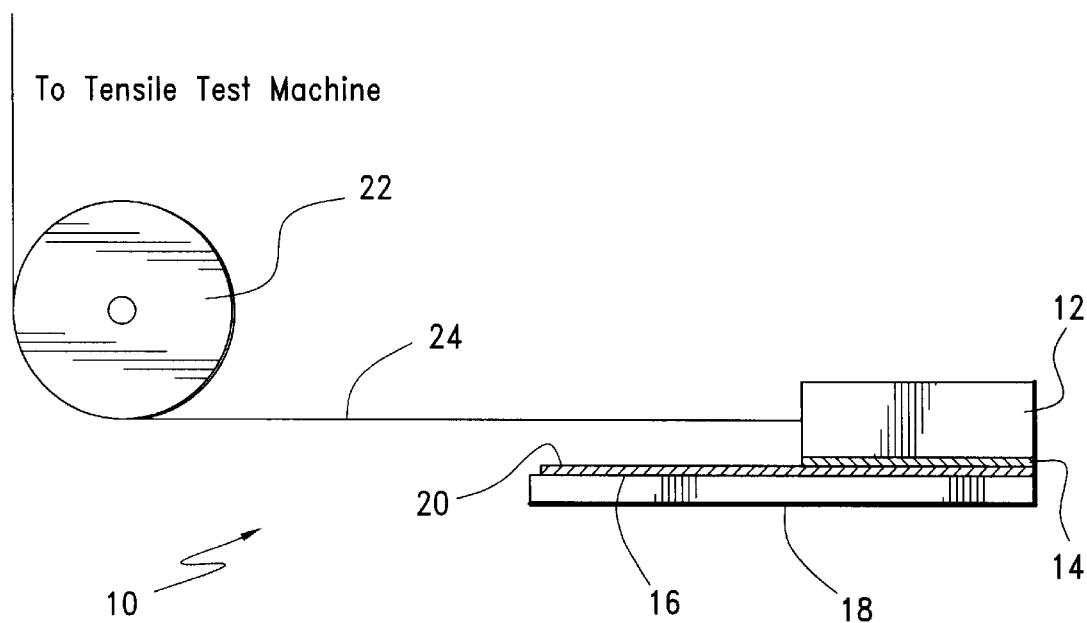
FIG. 1 illustrates an apparatus used for measuring the QE Value of a material.

The invention establishes a method for determining the relative hand quality of a fabric in comparison with other fabrics, but is also applicable to the grading of other materials, such as paper, polymers, and the like. The invention teaches a method including a new value which is useful for making this determination. The value is referred to as the Quality Energy Value (hereinafter the QE Value) of a material. The QE Value takes into account the reciprocatory motion actually used when rubbing a piece of fabric with a finger during a determination of the quality or hand of the fabric. The invention further utilizes a testing apparatus which simulates this motion of finger against cloth.

Friction Testing Apparatus

The apparatus that is used to measure the QE Value is illustrated schematically in FIG. 1. The apparatus 10 of FIG. 1 includes a wooden movable sledge 12 having a first swatch 14 of the fabric to be tested located on the bottom surface thereof. A stationary bottom aluminum sledge 16 is located on a stainless platform 18, and has a second swatch 20 of the fabric to be tested fixed on its upper surface. A frictionless pulley 22 is mounted at a distance from movable sledge 12, and an inextensible thread 24 is used to connect movable sledge 12 to an Instron crosshead (not shown), as is known in the art. The principle of the measurement was based on the rectilinear motion of a movable sledge 12 of area 12.25 cm$^2$ weighing 26.36 gms over stationary sledge 16. Movable sledge 12 was pulled at a constant speed of 50 mm/min by the Instron crosshead by means inextensible thread 24. The ratio of the chart speed to the crosshead speed was maintained at 1:1. The full-scale deflection of the machine was in the range 50–500 gms. The range of the pressure values used was between 220 Pa and 620 Pa.

Determination of QE Value

In the Description of the Prior Art, with respect to Equation (2), it was established that if the Frictional Force per unit area of contact (F) and the Normal Force per unit area of contact (P) are in units of Pa, then the friction constant C has a unit Pa$^{(1-n)}$. However, under the invention, when the values of C are raised to the power 1/(1-n), this creates a new constant having units of Pa. This constant will hereinafter be referred to as K, where $$K=C^{1/1-n} \quad (3)$$

Next, to take into account the speed of movement of the movable sledge 12 relative to the stationary sledge 16, K is multiplied by the velocity (V) of the movable sledge 12 relative to the stationary sledge 16 to produce the QE Value, thus:

$$\text{QE Value}=K(Pa)\times V(m/min) \quad (4)$$

The QE Value preferably has units of Joules/m$^2$ min, and, as will be demonstrated in more detail in the Examples below, it has been found that the lower the QE value, the higher the quality of the fabric. In addition, while the QE value is set forth in the preferred units of Joules/m$^2$ min, it will be apparent that other units will also work with the method of the invention, so long as comparisons of relative values are made using the same units.

In addition, Equation (4) may be reduced to the more basic components by which the QE value is measured. Accordingly, the QE value may also be described as $$QE=V\,(F/P^n)^{(1/1-n)} \quad (5)$$

wherein V is the velocity of movement of sledge 12 relative to stationary sledge 16, F is the measured frictional force, P is the normal force, and n is a frictional constant for that fabric in which 0<n<1. The usefulness and applications of the QE value are demonstrated in the following examples.

EXAMPLE 1

The experimental set-up described as above was used to characterize the frictional properties of a set of 1×1 rib knitted cotton fabrics (This experiment was conducted at the School of Textile Industries, University of Leeds, England). The details of the fabrics used in the investigation are given in Table I.

TABLE I

Details of Knitted Fabrics Used

| Fabric Code | NOMINAL LOOP LENGTH (cm) | YARN LINEAR DENSITY (Tex) | TIGHTNESS FACTOR (Tex$^{0.5}$cm$^{-1}$) | MASS (gm/m$^2$) |
|---|---|---|---|---|
| A | 0.285 | 29.5 | 19.0 | 287.4 |
| B | 0.306 | 29.5 | 17.7 | 271.4 |
| C | 0.326 | 29.5 | 16.6 | 256.7 |
| D | 0.350 | 29.5 | 15.5 | 238.9 |
| E | 0.368 | 29.5 | 14.7 | 215.7 |
| F | 0.267 | 22.7 | 17.8 | 231.9 |
| G | 0.285 | 22.7 | 16.7 | 226.3 |
| H | 0.306 | 22.7 | 15.5 | 200.6 |
| I | 0.275 | 18.4 | 15.6 | 188.5 |
| J | 0.303 | 18.4 | 14.1 | 177.8 |
| K | 0.318 | 18.4 | 13.5 | 162.1 |
| L | 0.275 | 16.4 | 14.7 | 160.3 |
| M | 0.303 | 16.4 | 13.3 | 149.1 |
| N | 0.318 | 16.4 | 12.7 | 142.1 |
| O | 0.275 | 14.0 | 13.6 | 145.8 |
| P | 0.303 | 14.0 | 12.3 | 128.5 |
| Q | 0.318 | 14.0 | 11.7 | 126.3 |

Results and Explanation

The new frictional constant K was used to calculate the QE values. The speed of sliding in this study was 0.05 m/min. QE values were used to characterize the frictional properties of knitted fabrics. The experimental results are given in Tables II and III.

TABLE II

Values of Frictional Constants

| Fabric Code | Frictional Constant K | | Friction Index n | |
|---|---|---|---|---|
| | Static (Pa) | Kinetic (Pa) | Static | Kinetic |
| A | 583.87 | 405.77 | 0.39 | 0.44 |
| B | 629.99 | 435.92 | 0.42 | 0.45 |
| C | 647.66 | 447.39 | 0.42 | 0.44 |
| D | 704.63 | 494.15 | 0.43 | 0.43 |
| E | 719.99 | 538.97 | 0.43 | 0.44 |
| F | 506.68 | 343.14 | 0.39 | 0.37 |
| G | 518.21 | 362.01 | 0.37 | 0.40 |
| H | 596.66 | 386.54 | 0.40 | 0.41 |
| I | 502.46 | 295.99 | 0.38 | 0.52 |
| J | 565.08 | 335.84 | 0.45 | 0.51 |
| K | 619.42 | 393.20 | 0.51 | 0.49 |
| L | 454.29 | 242.47 | 0.45 | 0.52 |
| M | 495.70 | 279.99 | 0.48 | 0.54 |
| N | 499.83 | 340.56 | 0.47 | 0.46 |
| O | 438.30 | 206.99 | 0.44 | 0.53 |
| P | 465.44 | 252.58 | 0.45 | 0.54 |
| Q | 502.88 | 283.44 | 0.46 | 0.51 |

TABLE III

QE Values

| | QE Values | |
|---|---|---|
| Fabric Code | Static | Kinetic |
| A | 29.19 | 20.29 |
| B | 31.50 | 21.80 |
| C | 32.38 | 22.35 |

TABLE III-continued

QE Values

| Fabric Code | QE Values | |
|---|---|---|
| | Static | Kinetic |
| D | 35.23 | 24.71 |
| E | 35.99 | 26.95 |
| F | 25.33 | 17.16 |
| G | 25.91 | 18.10 |
| H | 29.83 | 19.33 |
| I | 25.12 | 14.80 |
| J | 28.25 | 16.79 |
| K | 30.97 | 19.66 |
| L | 22.71 | 12.12 |
| M | 24.79 | 13.99 |
| N | 24.99 | 17.03 |
| O | 21.92 | 10.35 |
| P | 23.27 | 12.63 |
| Q | 25.14 | 14.17 |

Influence of Loop Length

It is evident from the experimental results that there is an increase in the QE values with an increase in loop length. In addition to the influence of loop length, yarn fineness also plays a very important role. For different yarn fineness values, the result obtained is similar, i.e., an increase in the loop length has a positive effect on the frictional constant values. Knitted fabrics are made up of a series of interconnected loops arranged in a regular pattern. The loops offer resistance to the smooth sliding motion of a fabric over another fabric due to the intermeshing of loops of the two fabrics. The shape and the size of the loops play a major part in offering resistance to the smooth motion. Generally, a fabric having a longer loop length is less tight. An increase in the loop length results in an increase in the waviness of the loops within the fabric structure and hence the resistance to sliding. As the fabric moves over another fabric, shearing and bending of the loops at the points of contact also takes place. Such deformations will be greater for a looser fabric than for a tighter fabric. This results in more energy dissipation to overcome the friction between fabrics. Furthermore, there will be greater deformation in the structure because of the looseness in the structure, which results in a greater amount of shearing at the contact points when sliding.

It has been well established (Howell and Mazur, 1953) that friction has two components, the adhesion and shearing components. In this particular case, the contribution due to the shearing of the joints to the frictional resistance is the greater. This is also evident from the results obtained by Harlock and Ramkumar ("A Study of the Handle Characteristics of Cotton Rib Knitted Fabrics", Proc. 78$^{th}$ World Conf. of the Text. Inst., 22, 149–161 (1997)) on the rigidity of knitted fabrics to shearing and bending deformations. In the case of polymers, it has been shown that the ploughing and shearing components dominate the frictional losses in rolling and sliding friction (Oshawa and Namiki, "Anistropy of the Static Friction of Plain-Woven Filament Fabrics", J. Textile Mach. Soc. Japan, 2(5), 197–203 (1966)). This explanation also supports the fact that an increase in the loop length results in an increase in the frictional resistance. As the normal load applied increases, the effect is exacerbated with increased crushing and shearing of loops.

One more possible explanation of this situation could be that, with an increase in the loop length, the intermeshing of loops of the sliding fabrics increases which results in an increase of adhesion between the two fabrics. As the adhesion increases, to keep the sliding process continuous, the adhesive junctions have to be sheared. This results in the expending of greater shearing energy, which ultimately results in greater frictional resistance of knitted fabrics.

Influence of Yarn Linear Density

Yarn fineness decides the diameter of the yarns and hence the area of contact between the two sliding fabrics' surfaces. The coarser is the yarn, the larger is the diameter than a finer yarn, provided that the twist in the yarns is more or less similar. As stated earlier, friction depends on the area of contact (Carr et al., 1988; Howell and Mazur, 1953). An increase in the area of contact results in an increase in the adhesion between two sliding surfaces. Adhesion between two coarse yarn fabrics is greater than the adhesion between two fine yarn fabrics. Hence, the resistance to motion is smaller for a fine yarn fabric than for a coarse yarn fabric. The results shown in Table II support this argument. It is interesting to note that both static and kinetic frictional constant values follow similar trends Furthermore, yarn linear density affects the mechanical properties of the yarns such as compression and friction. (Peirce, 1930; Wilson, 1963). Chattopadhyay and Banerjee ("The Frictional Behavior of Ring-, Rotor_, and Friction-Spun Yarn", J. Textile Inst., 81, 59–66 (1996)) have recently found that the compressibility of yarn plays a predominant role in affecting the frictional properties of yarns. Dupius et al. ("Compression of Greystate Fabrics as a Function of Yarn Structure", Textile Rs. J., 65, 309–316 (1995)) have recently reported that the compressibility of fabrics is dependent to a certain extent on the linear mass of the yarn from which they are made. The higher is the compressibility, the lower is the resistance offered to any kind of deformation. Experimental results obtained by Harlock and Ramkumar (1997) show that finer yarn fabrics are highly compressible. In addition, finer yarns offer less resistance to bending. Fabrics with high compressibility values offer less resistance to sliding motion and hence their frictional values are lower. It is evident from the experimental results that coarser yarn fabrics have higher frictional resistance. The result is similar for the different loop lengths investigated. It is also evident that both the static and kinetic frictional constant values follow the same trend.

In order to verify the usefulness and the validity of the new objective method, subjective hand evaluation was carried out. Twenty subjects who have adequate experience in this trade participated in the study. In general subjects felt it was a difficult exercise to rank the fabrics. The reason was that the variations in the constructional features of the fabrics investigated were not so greatly varied as to be easily subjectively discriminated. However, the overall conclusion of the test was that the tighter the fabric, the rougher the skin feel or hand of the fabric, and vice-versa. This corresponds with the results of Example 1 which demonstrate that tighter fabrics have higher QE values. Accordingly, fabrics having higher QE values were perceived as having poorer hand or poorer quality of fabric.

EXAMPLE 2

Another study was conducted to establish the versatility and universality of the new method, In this study 100% cotton fabrics were used. A plurality of swatches of the fabrics were subjected to enzyme finishing treatment. This treatment was given because it has been shown in the past that the enzymes enhance the perceived hand quality of the fabrics. This study demonstrated that the method the invention could distinguish the enzyme treated fabrics from the untreated fabrics and objectively quantify the improvement in the hand of fabrics by the enzyme treatment. Details of the fabrics used in this study are given in Table IV.

TABLE IV

Fabric Details

| Details | Nature/Value |
| --- | --- |
| Type | 100% Cotton |
| Ends/inch | 69.4 |
| Picks/inch | 74.8 |
| Warp Count (Ne) | 24.0 |
| Weft Count (Ne) | 23.3 |
| Weight (oz/sq. yard) | 4.2 |

Enzyme Application

Cellusoft™ AP (Novo Nordisk Biochem North America Inc.) was used in all the experiments. The enzyme application was done using a jigger. An Ernst Benz lab model jigger was used for the application of enzymes at a passage speed of 2 m/min in all the experiments. The time and the temperature of the treatment were maintained constant at 30 minutes and 50° C. Fabrics were treated with CellUSoft™ AP at six different concentration levels. The different concentration levels used are given in Table V.

TABLE V

Enzyme Concentration Levels

| Fabric Code | Enzyme Level (% owf) |
| --- | --- |
| A0 (control) | 0.0 |
| A1 | 0.5 |
| A2 | 1.0 |
| A3 | 1.5 |
| A4 | 3.0 |
| A5 | 5.0 |
| A6 | 10.0 |

Enzyme application details are given in Table VI.

TABLE VI

Process Details

| Process Details | Value |
| --- | --- |
| Weight of Sample (gms) | 82 |
| Concentration of Enzyme (% owf) | X (Table IV) |
| M:L Ratio | 1:20 |
| Wetting Agent (% owf) | 1 |
| Time of Treatment (min) | 30 |
| Temperature (° C.) | 50 |
| PH | 5 |

The enzyme application process was terminated by soaking the enzyme treated fabrics in water at a pH 8 at 80° C. for 10 minutes. Fabrics were then rinsed in cold water (5 times) and then dried in air.

Fabric Frictional Property Evaluation

As the primary objective of the study was to investigate the influence of cellulase enzymes on the surface mechanical properties of fabrics, frictional properties of enzyme treated fabrics were evaluated using the apparatus as shown in FIG. 1. Frictional properties of the fabrics were measured over a range of 5 different normal loads and were characterized using new QE value.

The experimental set-up for Example 2 was slightly altered from the set up of Example 1. This was intentionally carried out to examine if reliable and meaningful results would be obtained if the testing process variables were altered. In this study, a universal tensile tester manufactured by Shirley Developments Ltd., was used in place of the Instron. The speed of sliding was kept constant at 100 mm/min and the load cell capacity was 25 kgf. As mentioned above, the sliding experiment was conducted at 5 different normal loads—the minimum and the maximum loads were 36.54 and 76.54 gms respectively. The load was increased in steps of 10 gms. The apparent area of contact was 20 $cm^2$. A bovine leather sledge (a standard friction substrate) was used as movable sledge 12, rather than the fabric covered movable sledge 12 used in the first Example above. The fabrics to be tested were placed on stationary sledge 16, as in Example 1.

Experimental Results

Each sample was tested three times and at five different normal loads. The average friction force value at each normal load was used to obtain "C" and "n" values. Friction force and normal load values were used in Equation (2) to calculate the C and n values. The C and n values of untreated and enzyme treated fabrics are given in Table VII.

TABLE VII

Friction Parameter and Material Index Values

| Fabric Code | Friction Parameter "C" [$Pa^{(1-n)}$] | Material Index "n" |
| --- | --- | --- |
| A0 | 0.392 | 0.772 |
| A1 | 0.094 | 0.879 |
| A2 | 0.100 | 0.874 |
| A3 | 0.113 | 0.870 |
| A4 | 0.048 | 0.904 |
| A5 | 0.095 | 0.876 |
| A6 | 0.143 | 0.832 |

The C and n values were used to obtain the K values using Equation (3). K values were then multiplied by the velocity (V) to determine the QE values. QE values are given in Table VIII.

TABLE VIII

Fabric QE Values

| Fabric Code | Fabric QE Values |
| --- | --- |
| A0 | 0.002 |
| A1 | $3.30 \times 10^{-10}$ |
| A2 | $1.15 \times 10^{-9}$ |
| A3 | $5.22 \times 10^{-9}$ |
| A4 | $1.81 \times 10^{-15}$ |
| A5 | $5.76 \times 10^{-10}$ |
| A6 | $9.42 \times 10^{-7}$ |

Fabrics were ranked for their quality based on the QE values. Fabric ranks are given in Table IX.

TABLE IX

Fabric Ranks

| Fabric Code | Fabric Ranks |
| --- | --- |
| A0 | 1 |
| A1 | 6 |
| A2 | 4 |
| A3 | 3 |
| A4 | 7 |
| A5 | 5 |
| A6 | 2 |

As is evident from Table IX enzyme treated fabrics all performed had QE values lower than that of the untreated fabric. To prove the validity of the new objective method, a subjective evaluation was undertaken. These fabrics were rated subjectively by people in the trade. Overall consensus was that the enzyme treated fabrics were observed to be smoother and better in hand than the untreated fabric A0. However subjects felt it was extremely diffiucult to distinguish among enzyme treated fabrics. But, it was possible to successively grade fabrics using the new method. The results confirm that the new method is simple, reliable and applicable.

Accordingly, while foregoing examples demonstrate exemplary features of the present invention, it will be apparent to those skilled in the art that a number of changes to the preferred embodiments may be made while still remaining within the scope of the invention and its equivalents, as set forth below in the claims.

What is claimed:

1. A method for determining the relative quality of a fabric having a frictional index n, said method comprising:
    applying a predetermined normal force P to a fabric in contact with a surface over a predetermined area:
    measuring a frictional force F by moving the fabric relative to the surface at a predetermined velocity V;
    determining a fabric quality value QE for the fabric wherein
    QE=KV, wherein $K=C^{(1/1-n)}$ and $C=F/P^n$; and
    repeating said foregoing steps for a plurality of fabrics to determine a range of QE values for said plurality of fabrics, whereby those fabrics having relatively lower values have a higher hand quality.

2. The method of claim 1 further including the step of providing a movable sledge and a stationary sledge, and applying said normal force to said movable sledge and pulling said sledge to measure said frictional force.

3. The method of claim 1 further including the step of fixing a second piece of said fabric to said surface, whereby said fabric moves against said second piece of said fabric.

4. A method for determining the relative frictional properties of a plurality of materials, said method comprising:
    placing a piece of said material in contact with a surface;
    applying a normal load P to the material and the surface;
    moving said material relative to said surface at a constant velocity V, while measuring the frictional force F; and
    establishing a QE value for the material wherein QE is determined by $$QE=V(F/P^n)^{(1/1-n)}$$

wherein n is a frictional index having a value between 0 and 1 for the material being graded; and
    repeating the foregoing steps for each of said plurality of materials whereby the materials having the large QE values are graded as having a lower hand quality than those having a lower QE value.

5. A method for determining the hand quality of each of a plurality of fabrics each having a frictional index n, said method comprising:
    providing a sledge apparatus including a movable sledge;
    using said sledge apparatus and applying a predetermined normal force P to the fabric;
    moving said movable sledge of said sledge apparatus at a constant velocity V relative to the fabric whose hand quality is to be determined to determine a frictional force F for the fabric;
    determining a friction parameter K for said fabric wherein $K=C^{1/1-n}$ and $C=F/P^n$;
    multiplying said friction parameter K by the constant velocity V of the sledge to obtain a QE value for each fabric; and
    ranking the fabrics according to said QE values, whereby the relative quality of each fabric's ranking is related to the QE value of that fabric.

* * * * *